United States Patent [19]
Campbell

[11] Patent Number: 5,836,907
[45] Date of Patent: Nov. 17, 1998

[54] DISPOSABLE GASTRIC LAVAGE KIT

[76] Inventor: Sharon L. Campbell, 4075 Seven Hills Ct., Stone Mt., Ga. 30083

[21] Appl. No.: 743,821

[22] Filed: Nov. 5, 1996

[51] Int. Cl.$^6$ .................................................. A61M 1/00
[52] U.S. Cl. ............................................................ 604/27
[58] Field of Search ............................ 604/80, 81, 82, 604/30, 35, 257, 27, 408, 409, 410, 903, 131, 262, 403, 905

[56] References Cited

U.S. PATENT DOCUMENTS

| | | |
|---|---|---|
| 4,114,625 | 9/1978 | Onat . |
| 4,368,729 | 1/1983 | Dossin . |
| 4,525,156 | 6/1985 | Benusa et al. . |
| 4,639,251 | 1/1987 | Kirkland . |
| 5,405,333 | 4/1995 | Richmond ............................... 604/257 |
| 5,492,531 | 2/1996 | Post et al. . |

*Primary Examiner*—Manuel Mendez
*Attorney, Agent, or Firm*—Spencer & Frank

[57] ABSTRACT

A disposable gastric lavage assembly includes at least one fluid receiving container having an upper end and a lower end, a first self-sealing port located in a region of the upper end, and a second self-sealing port located in a region of the lower end. A flexible tubing is provided that has at least first and second ends, with the second end being connectable to one of a nasogastric and orogastric adapter located within a nose or mouth, respectively, of a patient. At least one breaching device is connected to the first end of the tubing for breaching a selected one of the self-sealing ports so that an interior of the container is in fluid communication with an interior of the tubing. A method is also proposed that utilizes the assembly for performing a lavage on a patient.

15 Claims, 3 Drawing Sheets

DISPOSABLE GASTRIC LAVAGE KIT

BACKGROUND OF THE INVENTION

The present invention relates to a disposable gastric lavage assembly. More particularly, the present invention relates to an assembly used for lavaging a gastrointestinal cavity of a patient, and a method of doing the same.

Gastric lavages performed by emergency personnel may be necessary for various reasons. For example, if a harmful substance such as a poison is ingested by a person, a gastric lavage may be necessary to remove the substance from the gastrointestinal cavity of the person.

Moreover, it may be necessary to lavage the gastrointestinal cavity of a patient with an additive to neutralize an ingested toxic substance. For example, it may be desirable to counteract the effects of the toxic substance by introducing into the gastrointestinal cavity a highly absorbent activated carbon or charcoal solution to absorb the ingested toxic substance.

Further, in the case of gastrointestinal bleeding, lavaging may be necessary to remove the blood from the stomach. In the situation of severe gastrointestinal bleeding, an ice water lavage might be necessary to help slow down the bleeding.

Various apparatuses and methods for introducing a solution into the gastrointestinal cavity of a patient are known. For example, it is known to provide a stomach lavage apparatus for the introduction of a highly absorbent antidote solution, such as activated charcoal, into the gastrointestinal cavity for the purpose of absorbing or otherwise counteracting a digested poison present therein. However, these known devices are typically complex and expensive, and may allow only for the introduction of a fluid or antidote into the gastrointestinal cavity of the patient. For the introduced fluids to be removed from the gastrointestinal cavity, a separate assembly typically needs to be provided, such as a suction machine, which aspirates the fluids from the gastrointestinal cavity using a generated vacuum. However, in the case of gastrointestinal bleeding, suction machines pose the risk of increasing the bleeding within the gastrointestinal cavity. Moreover, suction machines typically require a source of power, hindering the portability of the machine. Further, as will be appreciated, the use of a suction machine (or any device separate from the device used to introduce the fluids into the gastrointestinal cavity of the patient) significantly increases the cost of the lavaging procedure.

Further, it is known to modify devices intended for other purposes, so that the introduced fluids can be removed from the gastrointestinal cavity. For example, it is known to utilize a known foley bag, which is normally configured to be attached to a foley catheter for the collection of urine. However, when a foley-type bag is used, it must be specially modified for attachment to a nasogastric or orogastric adapter which is attached to a patient. However, such adaption is time consuming, which may prove to be fatal during emergency situations. Further, such a modified device, even when adapted for connection to a nasogastric or orogastric adapter, is not suitable for both the infusion and the collection of fluids to and from the gastrointestinal cavity of the patient. This is because there are different considerations that must be taken into account when infusing a fluid into the gastrointestinal cavity of the patient as opposed to the collection of such fluids.

SUMMARY OF THE INVENTION

It is an object of the present invention to provide an apparatus that is specifically configured for the infusion and collection of a fluid to and from a gastrointestinal cavity of a patient.

It is a further object of the present invention to provide a method of lavaging a gastrointestinal cavity of a patient in which a fluid is introduced into the gastrointestinal cavity of the patient, and collected therefrom.

The above and other objects are accomplished according to the invention by the provision of a disposable gastric lavage assembly that includes at least one fluid receiving container having an upper end and a lower end. The container further includes a first self-sealing port located in a region of the upper end of the container and a second self-sealing port located in a region of the lower end of the container.

A flexible tubing is provided that has first and second ends. The second end of the tubing is connectable to either a nasogastric or orogastric adapter which is located within a nose or mouth, respectively, of a patient.

At least one breaching device is connected to the first end of the tubing for breaching a selected one of the self-sealing ports so that an interior of the container is in fluid communication with an interior of the tubing.

This configuration provides for an assembly that includes a container that can be used for introducing a fluid into the gastrointestinal cavity of a patient by connecting the flexible tubing to the lower self-sealing port, and which allows the fluid to be collected from the gastrointestinal cavity of the patient by connecting the flexible tubing to the upper self-sealing port.

When the fluid is to be introduced into the gastrointestinal cavity of the patient, the container is raised to an elevation above the gastrointestinal cavity of the patient, and the breaching device is attached to the second self-sealing port which is located in a region of the lower end of the container. Connection to this particular self-sealing port will allow essentially all of the fluid within the container to drain into the gastrointestinal cavity of the patient.

Once the container is empty, the breaching device can be removed from the second self-sealing port. Because the port is self-sealing, any fluid remaining within the container is contained therein, and will not leak or spill out.

The container is then lowered to a height below the gastrointestinal cavity of the patient, and the breaching device is connected to the first self-sealing port which is located in a region of the upper end of the container, to allow the fluid introduced into the gastrointestinal cavity (together with any blood or toxic substances therein) to be drained back into the container.

This connection and arrangement helps to ensure that any of the toxic fluids collected within the container will not be reintroduced into the gastrointestinal cavity, since the first (upper) self-sealing port will be located at a position above a fluid level within the container.

Further, during the drainage of the gastrointestinal cavity, the second self-sealing port (which is located in a region of the lower end of the container) is available for use by a physician or other emergency personnel so that contaminated fluids can be safely collected by securing a tip of a syringe to this port and aspirating the fluid within the container into the syringe for storage and/or testing.

Moreover, during the drainage of the fluid from the gastrointestinal cavity, because the tubing is connected to the first (upper) self-sealing port, the flow of the fluid from the tubing and into the container is more visually apparent, since the contaminated fluid will fall (either in a stream or in drips) from the first self-sealing port through the container and into the fluid collected in the bottom thereof. Thus, should the flow of fluid cease, this will be readily apparent due to the absence of the stream or drips of the fluid through the container. If, on the other hand, the tubing were collected to the lower self-sealing port during the drainage of the gastrointestinal cavity, the emergency personnel would be reliant strictly upon the apparent increase of fluid within the bag, which may be difficult to ascertain at any particular point in time, especially as the flow of fluid begins to slow down.

Further, instead of one container, two containers can be provided, and the tubing can be provided with an essentially Y-shaped configuration having three ends. A first breaching device is attached to one of the ends of the tubing for connection with a first (upper) self-sealing port of one of the containers, and a second breaching device can be attached to another one of the ends of the tubing for connection with a second (lower) self-sealing port of the other one of the containers.

This configuration is advantageous in that the tubing does not need to be removed from one port and attached to the other port during the lavage of the patient, which may provide for more rapid lavaging of the gastrointestinal cavity. Moreover, since the two containers are preferably identical, during set up of the apparatus, there is no possibility that the wrong bag will be attached to the wrong branch of the tubing. Further, and as will be appreciated, it is less expensive to manufacture two identical bags, rather than two bags of different design.

Preferably, the container includes a resealable opening at the upper end thereof for filling the container with a liquid and, if necessary, additives. The resealable opening preferably comprises either a number of snap seals or a zipper-type seal that can be opened to allow for the easy introduction of the necessary fluid and/or additives. This feature allows the fluid and/or additives to be introduced into the container with a reduced risk of spillage, while still allowing the container to be sealed against outside contaminants and to prevent the contents of the container from spilling out of the container.

The container further has a series of graduated markings on a surface thereof, which are indicative of a volume of the liquid within the container. Because the container remains in the same relative orientation during both the introduction of the fluid into the patient and the receiving of the fluid from the patient, the markings can be used to indicate both the amount of fluid introduced into the patient, as well as the amount of fluid drained back into the container.

The assembly preferably includes a check valve located within the tubing. The check valve allows the fluid to flow in only one direction, thus preventing a back flow of contaminated fluid back into the container. Further, the check valve is preferably reversible, so that the fluid flow is selectable and changeable, so as to allow the fluid to only flow back into the container from the patient, as appropriate.

The self-sealing ports preferably comprise either a seal composed of either plastic or rubber, which seal is breached using a hollow spike that is attached to an end of the tubing, and that is insertable through the seal to establish the fluid communication between the interior of the container and the interior of the tubing. This configuration is relatively reliable and inexpensive, since there are no moving parts involved. Because the rubber or plastic has a memory, when the spike is removed, the point of insertion through the seal closes automatically, thus preventing any fluids within the container from leaking therefrom.

Alternatively, the self-sealing ports can include a valve that is breachable by a breaching device that is attached to the end of the tubing. The breaching device attached to the end of the tubing is insertable into the valve to open the valve and establish the necessary fluid communication. This type of port may provide a more secure seal once the breaching device is removed, to positively ensure that fluid within the container does not leak out.

The breaching device at the end of the tubing can be provided with a locking device which is engageable with the valve (such as a bayonet-type mount as is known in the art), so as to positively lock the two components together. This type of arrangement may be desirable when there is a possibility of the inadvertent removal of the tubing from the container.

The present invention further provides for a method of lavaging a gastrointestinal cavity of a patient. The method includes the steps of providing a container having an upper end and a lower end, and a first self-sealing port located in a region of the upper end of the container. A second self-sealing port is located in a region of the lower end of the container. A flexible tubing is provided having first and second ends. A breaching device is connected to the first end of the tubing for breaching a selected one of the self-sealing ports so that an interior of the container is in fluid communication with an interior of the tubing.

The container is preferably first filled with a fluid used for lavaging the gastrointestinal cavity of the patient. The container is positioned at an elevation above the patient, and the flexible tubing is closed. The second end of the tubing is connected to a nasogastric or orogastric adapter located within a nose or mouth, respectively, of a patient.

The second self-sealing port is breached with the breaching device to establish the fluid communication between the interior of the container and the interior of the tubing. The flexible tubing is unclamped to allow the fluid to flow from the container into the gastrointestinal cavity of the patient.

The flexible tubing is then reclamped closed, and the container is lowered to a position lower than the gastrointestinal cavity of the patient. The tubing is detached from the second self-sealing port, and the first self-sealing port is breached with the breaching device to re-establish the fluid communication between the interior of the container and the interior of the tubing. The flexible tubing is then unclamped to allow the fluid to flow from the gastrointestinal cavity of the patient into the container.

This particular method provides for a safe and effective lavaging of the gastrointestinal cavity of a patient, and which is suitable for emergency situations. This method may be preferred where lavages with a longer stasis time are required, or where a compact assembly is required.

Further, the present invention provides for a method in which two containers are provided, with the first container being positioned at an elevation above the patient and the second container being positioned at an elevation below the gastrointestinal cavity of the patient.

The first container is filled with fluid, and a flexible, Y-shaped tubing (having first, second and third ends) is closed by clamping the tubing in regions of both its first and second ends (each of which has a breaching device connected thereto). The third end of the tubing is connected to the nasogastric or orogastric adapter located within the nose or mouth, respectively, of the patient.

The second (lower) self-sealing port of the first (raised) container is breached using one of the breaching devices to establish the fluid communication between the interior of the first container and the interior of the tubing. Further, the first (upper) self-sealing port of the second (lowered) container is breached using the other breaching device.

The flexible tubing is unclamped in a region of the first end to allow the fluid to flow from the first container into the gastrointestinal cavity of the patient. Next, the flexible tubing is unclamped in a region of the second end to allow the fluid to flow from the gastrointestinal cavity of the patient and into the second container.

This particular method provides for the lavaging of a gastrointestinal cavity of a patient in a safe and effective manner, and which may be used for constant non-stop lavaging, and lavaging with a reduced stasis time. Further, this method can be used for emergent lavages.

The invention will now be described below in greater detail in connection with embodiments thereof that are illustrated in the drawing Figures.

DETAILED DESCRIPTION OF THE INVENTION

Figure 1:
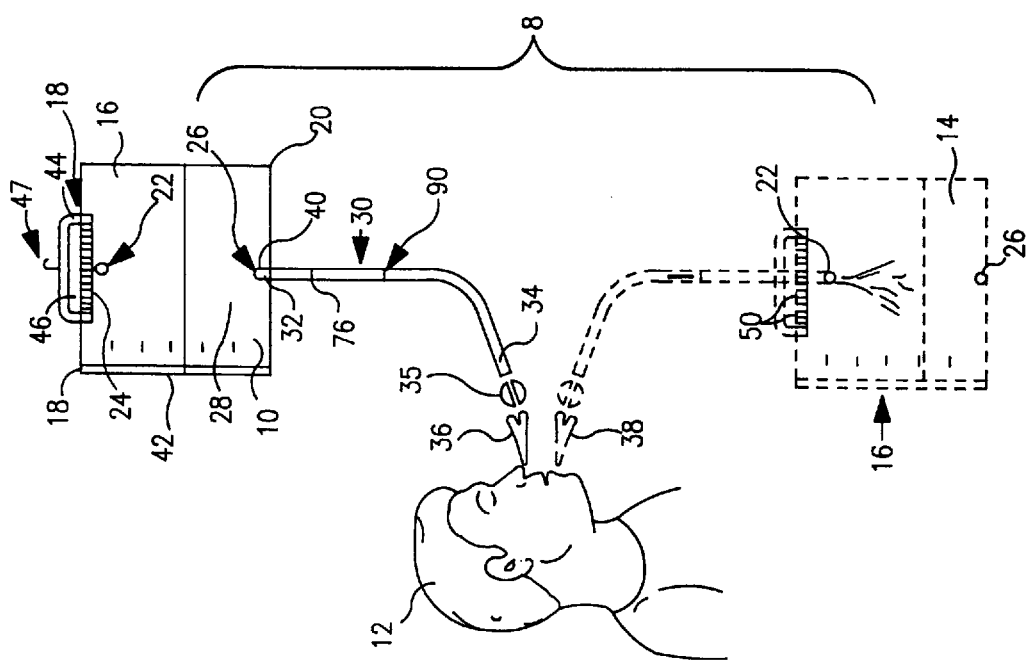
FIG. 1 is an illustration of a gastric lavage assembly according to the present invention being used on a patient.

Referring generally to FIG. 1, a disposable gastric lavage assembly 8 according to the present invention is illustrated. This illustration shows the assembly 8 in a raised position, indicated by solid lines, for the infusion of a liquid 10 into the gastrointestinal cavity (not shown) of a patient 12. The figure also shows in hidden lines the lavage assembly 8 in a lowered position for collection of the contaminated fluids 14 from the patient's gastrointestinal cavity.

The lavage assembly 8 generally includes at least one fluid receiving container 16. The fluid receiving container 16 has an upper end 18 and a lower end 20. A first self-sealing port 22 is located in a region 24 of the upper end 18, and a second self-sealing port 26 is located in a region 28 of the lower end 20.

A flexible tubing 30 is provided that has at least a first end 32 and a second end 34. The second end 34 of the flexible tubing 30 is connectable via a connector 35 to either a nasogastric 36 or orogastric 38 adapter located within the nose or mouth, respectively, of patient 12.

A breaching device 40 (shown only schematically in this figure) is connected to the first end 32 of the tubing 30 for breaching a selected one of the self-sealing ports 22, 26 so that the interior of the container 16 is in fluid communication with the interior of the tubing 30.

The fluid receiving container 16 preferably holds between about 2 to 4 liters of liquid 10, which is used to flush the gastrointestinal cavity of the patient 12 as will be described in detail later. The liquid 10 can comprise ice, water, saline solution and other medically acceptable solutions. The container 16 may comprise opposed sheets of a flexible material, for example a clear plastic material such as polyvinyl chloride (PVC) film of between about 4 to 8 mils thickness, that can be heat sealed or otherwise joined along their common peripheries. Alternatively, the container 16 can be comprised of glass or other materials.

A plurality of graduated scale marks 42 having embossed numerical indices (not shown) provided thereon extend along a lateral edge or side of the container and serve as a liquid level indicator.

The upper end 18 of the container has a tab 44 having an opening or aperture 46 formed therein so that the tab can serve as a handle for hanging the container from, for example, a hook 47 or an intravenous stand (not shown). Alternatively, a separate handle (not shown) can be provided that is attached to the container 16. For example, if the container is comprised of glass, the container can be provided with a separate metal or plastic handle that is separately attachable to the upper end 18 of the container. The handle allows the container 16 to be hung in an upright position so that the fluid may be drained from the container through the lower self-sealing port 26, and drained into the container through the upper self-sealing port 22.

Figure 2:
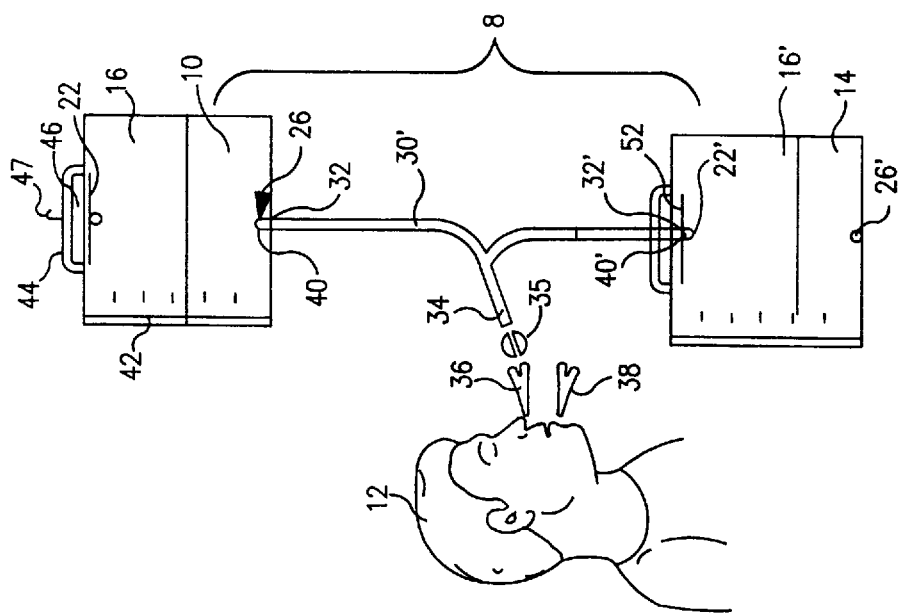
FIG. 2 is an alternative embodiment of the gastric lavage assembly according to the invention being used to lavage a patient.

The upper end 18 of the container 16 is provided with a resealable opening 48 so that the container can be filled with a liquid or additives, as necessary. In this figure, the opening is resealable using a plurality of snaps seals 50 which snap the two opposing sheets of flexible material together. Alternatively, the opening 48 can be provided with a zipper-type seal 52, such as shown in FIG. 2, which allows the opening to be zippered open and shut.

The tubing 30 is preferably comprised of a flexible plastic material, such as polyvinyl chloride, and is connectable at its ends 32, 34 to the breaching device 40 and nasogastric 36 or orogastric adapter 38 in a liquid tight manner. As shown in this figure, the tubing can comprise a single piece of tubing. However, as shown in FIG. 2, the tubing 30' can likewise have a Y- or T-shape, so that the tubing has three different ends 32, 32', 34, with end 34 being connectable to the nasogastric or orogastric adapter, and the ends 32, 32' being connected to two separate breaching devices 40, 40' for connection to two separate fluid receiving containers 16, 16'. The tubing 30' can be integrally formed into the necessary shape, or can be provided with a Y-shaped or T-shaped adapter (not shown) which would allow three separate pieces of tubing to be attached thereto.

Figure 3:
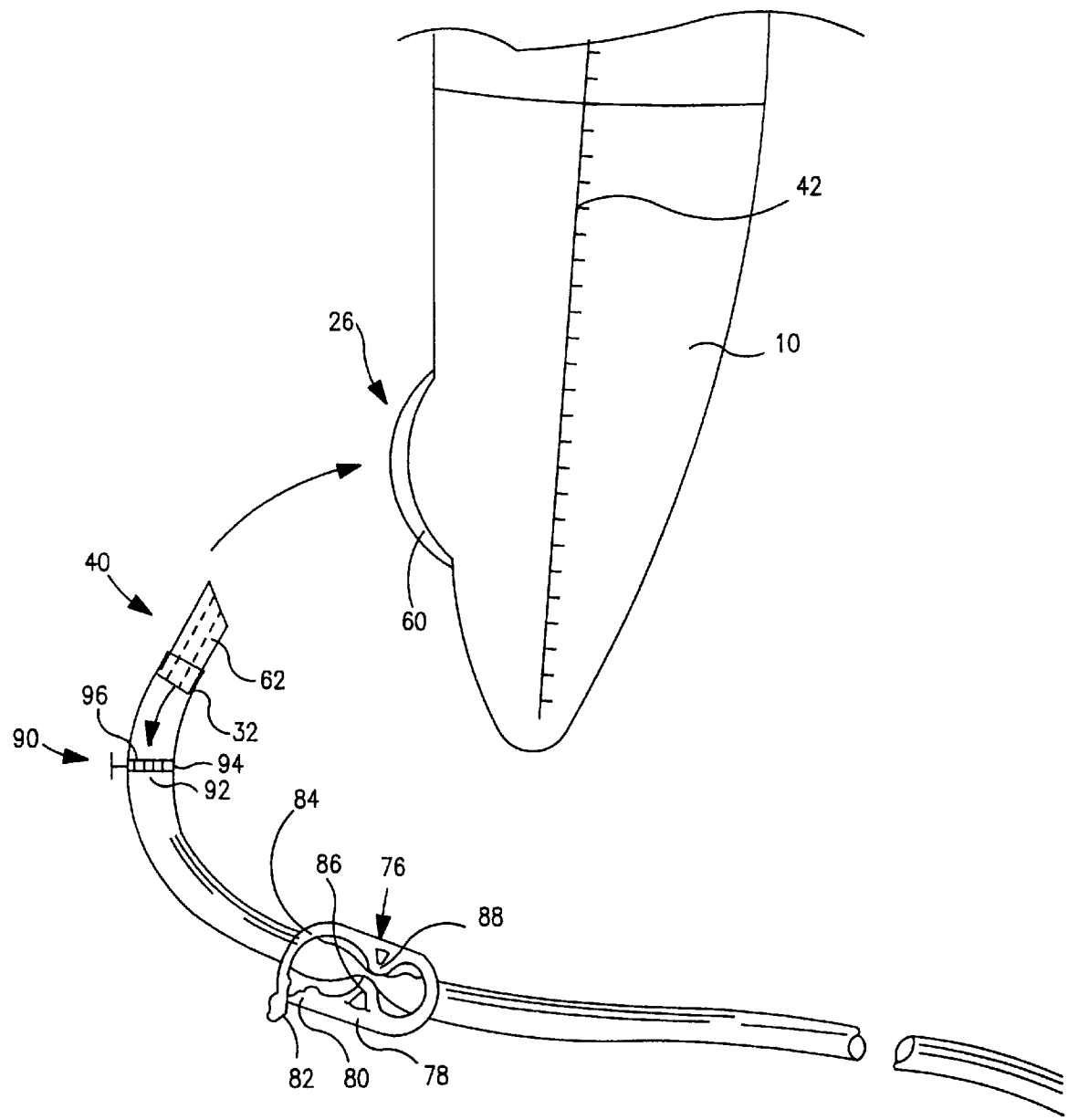
FIG. 3 is a partial view of the end of a tubing prior to the breaching of a self-sealing port, according to the present invention.

Referring now to FIG. 3, the self-sealing ports 22, 26 (only port 26 being shown) can comprise a seal 60 formed of a plastic or rubber material which is puncturable by a spike 62 that is attached to the end 32, 32' of the tubing. The material is selected so as to provide a seal with a memory, so that when the spike 62 is removed from the seal 60, the seal closes the opening made by the spike in a liquid-tight manner to prevent spillage of the fluid from within the container.

Figure 4:
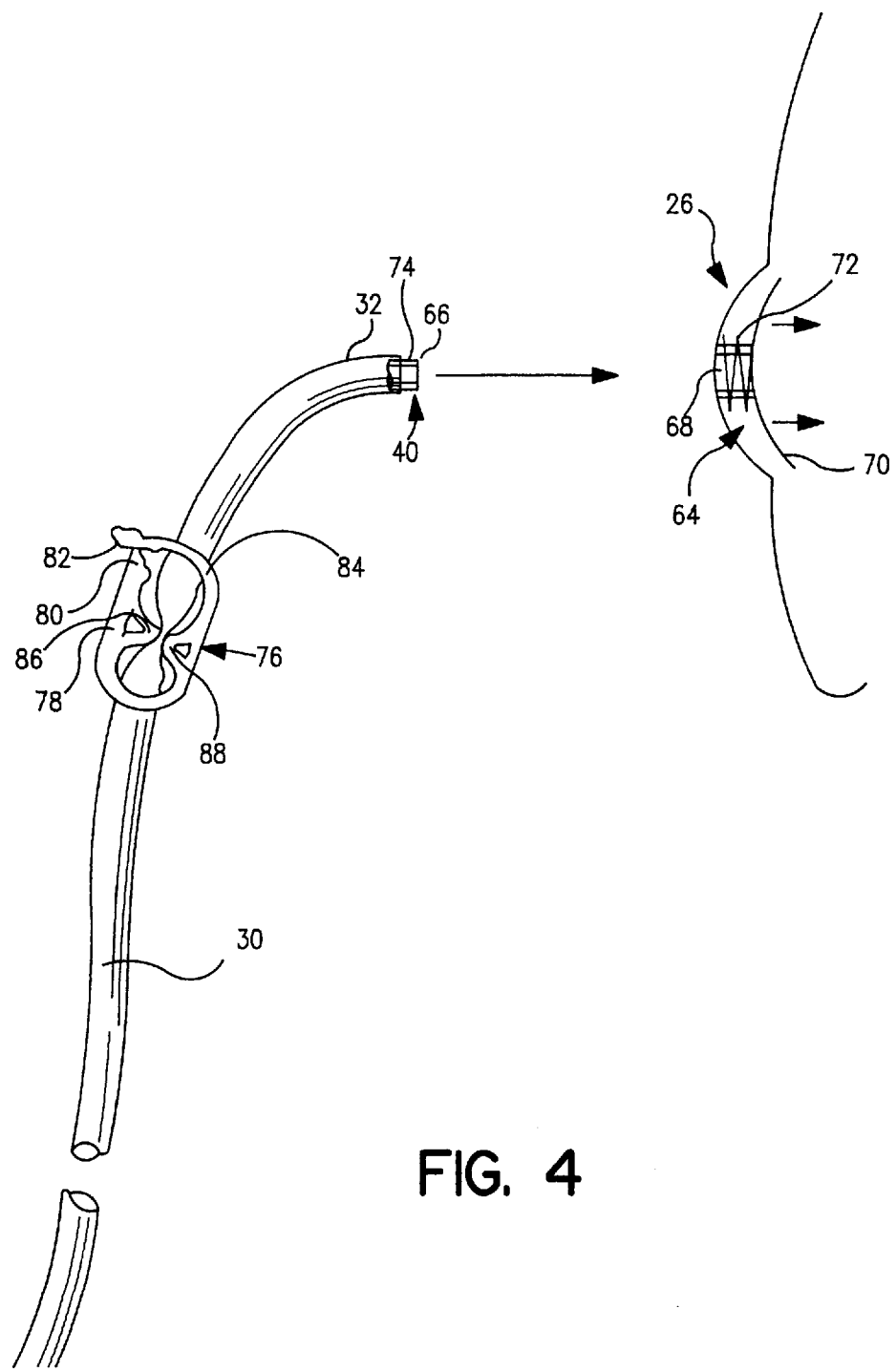
FIG. 4 is an alternative embodiment of the breaching device and self-sealing port according to the present invention.

As shown in FIG. 4, the resealable port 22, 26 (only port 26 being shown) can instead comprise a valve 64 that is actuated by a male adapter 66 attached to the end 32, 32' of the tubing. When the male adapter 66 is inserted into a female plug 68 of the valve 64, a valve seal 70 is urged in the direction of the arrows allowing fluid to pass through the port. When the male adapter 66 is removed from the port, a spring 72 urges the valve seal 70 in a direction opposite to the arrows, thus closing the port in a liquid-tight manner. The male adapter 66 and the female plug 68 can be provided with a locking device, such as a bayonet mount assembly 74, so that when the male adapter is inserted within the female plug, the tubing cannot be inadvertently removed.

As shown, the tubing 30 is provided a clamp 76 for closing the tubing to prevent fluid from flowing therethrough. The clamp 76 can comprise an adjustable clamp positioned on the tubing which can constrict the tubing to regulate the flow therethrough or close the tubing to prevent fluid flow entirely. The clamp 76 shown is a unitary member having a generally D-shaped configuration provided by a first leg 78 having a pawl 80 that is in a releasable locking engagement with ratchet teeth 82 provided on a second leg 84 of the clamp. The first leg 78 and second leg 84 of the clamp are further each provided with opposed, inwardly extending tabs 86, 88 that define opposing movable surfaces located on opposite sides of the tubing. The tabs 86, 88 serve to pinch the tubing 30, thereby constricting or otherwise stopping the fluid flow therethrough when the pawl 80 is engaged with the ratchet teeth 82.

However, instead of the clamp shown, other clamping devices can be used such as are known in the medical field. For example, disposable hemostats (not shown) could likewise be used to clamp the tubing shut.

As shown in FIG. 3, the tubing 30 is preferably provided with a reversible check valve 90 therein so as to allow fluid flow in only one direction through the tubing. The check valve 90 may include a seal 92 on one side of a base body 94. The base body has bores 96 or passages formed therein, extending from one side of the base body to the other side of the base body. The seal 92 allows the passage of the fluid through the bores of the base body in only direction. Further, the seal 92 and/or the base body 94 may be reversible so that the fluid can flow through the tubing in only a selected one of two directions.

In use, and referring generally to FIG. 1, an emergency technician would generally fill the container 16 with a fluid 10 used to lavage the gastrointestinal cavity of the patient 12. As noted earlier, the container 16 is preferably filled through the resealable opening 48, which allows the container to be filled in a relatively easy manner. After filling, the opening 48 is sealed shut using either the zipper seal 52 or the snap seals 50.

The emergency technician then hangs the container 16 at an elevated position higher than the gastrointestinal cavity of the patient 12. For example, the container could be hung from an IV stand using the handle.

The emergency technician next would take the tubing 30 and clamp the tubing closed using the clamp 76. One end 34 of the tubing 30 would be connected to the nasogastric or orogastric adapter which has been inserted within the nose or mouth of the patient. The other end 32 of the tubing 30, which has a breaching device 40 attached thereto, is then connected to the lower self-sealing port 26. In the process, the breaching device 40 breaches the self-sealing port 26 to establish a fluid communication between the interior of the container and the interior of the tubing.

Next, the emergency technician would unclamp the flexible tubing 30 to allow the fluid 10 to flow under the force of gravity from the container 16 into the gastrointestinal cavity of the patient. Once the desired amount of fluid has flowed into the patient's gastrointestinal cavity, the emergency technician would clamp the tubing closed again.

The container 16 is next positioned at a location that is lower than the gastrointestinal cavity of the patient, and the tubing 30 is detached from the lower self-sealing port 26. Further, if the tubing is provided with a check valve 90, such check valve would be reversed at this point.

The upper self-sealing port 22 of the container is then breached with the breaching device 40 to re-establish the fluid communication between the interior of the container and interior of the tubing.

After the proper stasis period has passed, the flexible tubing 30 is unclamped to allow the contaminated fluid 14 to flow from the gastrointestinal cavity into the container 16. During this period, should a physician desire to withdraw a sample of the fluid for testing purposes, such could be accomplished by attaching a syringe (not shown) to the now free lower self-sealing port 26 and drawing such a sample.

Once the flow of fluid stops (as is visually apparent from the absence of a fluid flow from the tubing 30 into the container 16), the tubing can be reclamped and detached from the upper self-sealing port 22 so that the container and the contaminated liquid can be disposed of.

Alternatively, instead of using one container 16 for both the drainage and the collection of the fluid, two separate (and preferably identical) containers 16, 16' can be utilized, each being connected to respective legs of a Y-shaped tubing 30'. Using this configuration, a first one of the containers 16 is filled with the fluid 10 and positioned at an elevation above the patient 12. The second container 16' is positioned at an elevation below the gastrointestinal cavity of the patient. The flexible tubing 30' is next clamped shut in regions of both its first and second ends 32, 32', i.e., at locations near the breaching devices 40, 40'. A free end 34 of the tubing is attached to the nasogastric or orogastric adapter located within the nose or mouth of the patient.

The lower self-sealing port 26 of the raised container 16 is breached with a breaching device 40, and the upper self-sealing port 22' of the lowered container 16' is breached with the other breaching device 40' to establish a fluid communication between the interior of the two containers and the interior of the tubing 30'.

The flexible tubing 30' is next unclamped in a region of the raised container 16, while remaining clamped in a region of the lowered container 16', to allow the fluid to flow from the raised container into the gastrointestinal cavity of the patient. Once the desired amount of fluid has flowed into the gastrointestinal cavity of the patient, the tubing 30' in a region in the lowered container 16' is unclamped to allow the fluid to flow from the gastrointestinal cavity of the patient into the second container. This method provides for a completely closed system for both the infusion of fluids, as well as the drainage of contaminated fluids via gravity. When the infusion and/or drainage is complete, the bags may be disposed of in a safe and sanitary manner.

The invention now being fully described, it will be apparent to one of ordinary skill in the art that any changes and modifications can be made thereto without departing from the spirit or scope of the invention as set forth in the claims below.

What is claimed is:

1. A method of lavaging a gastrointestinal cavity of a patient, comprising the steps of:

providing two containers, each having an upper end and a lower end, a first self-sealing port located in a region of the upper end of the container, and a second self-sealing port located in a region of the lower end of the container; a flexible, essentially Y-shaped tubing having first, second and third ends; and at least two breaching devices for breaching selected ones of said self-sealing ports, with a first one of the breaching devices being attached to the first end of the tubing, and a second one of the breaching devices being attached to the second end of the tubing;

filling a first one of the containers with a fluid;

positioning the first container at an elevation above the patient;

positioning the second container at an elevation below the gastrointestinal cavity of the patient;

clamping the flexible tubing closed in regions of both the first and second ends;

connecting the third end of the tubing to one of a nasogastric and orogastric adapter located within a nose or mouth, respectively, of the patient;

breaching the second self-sealing port of the first container with the first breaching device to establish a fluid communication between an interior of the first container and an interior of the tubing;

breaching the first self-sealing port of the second container with the second breaching device to establish a fluid communication between an interior of the second container and the interior of the tubing;

unclamping the flexible tubing in the region of the first end to allow the fluid to flow from the first container into the gastrointestinal cavity of the patient; and unclamping the flexible tubing in the region of the second end to allow the fluid to flow from the gastrointestinal cavity of the patient into the second container.

2. A method of lavaging a gastrointestinal cavity of a patient, comprising the steps of:

providing a container having an upper end and a lower end, a first self-sealing port located in a region of the upper end of the container, and a second self-sealing port located in a region of the lower end of the container; a flexible tubing having first and second ends; and a breaching device connected to the first end of said tubing for breaching a selected one of the self-sealing ports so that an interior of the container is in fluid communication with an interior of the tubing;

filling the container with a fluid;

positioning the container at an elevation above the patient;

clamping the flexible tubing closed;

connecting the second end of the tubing to one of a nasogastric and orogastric adapter located within a nose or mouth, respectively, of the patient;

breaching the second self-sealing port with the breaching device to establish the fluid communication between the interior of the container and the interior of the tubing;

unclamping the flexible tubing to allow the fluid to flow from the container into the gastrointestinal cavity of the patient;

reclamping the flexible tubing closed;

lowering the container to a position lower than the gastrointestinal cavity of the patient;

detaching the tubing from the second self-sealing port;

breaching the first self-sealing port with the breaching device to reestablish the fluid communication between the interior of the container and the interior of the tubing; and unclamping the flexible tubing to allow the fluid to flow from the gastrointestinal cavity of the patient into the container.

3. The method of ravaging defined in claim 2, said container further comprising sealing means engageable with said tubing for sealing said tubing to prevent a fluid from flowing therethrough.

4. The method of lavaging defined in claim 3, wherein said sealing means comprises a lockable clamp having two opposing movable surfaces locatable on opposite sides of said tubing and being movable toward each other to pinch said tubing closed.

5. The method of lavaging defined in claim 2, said container further comprising a check valve located within said tubing, said check valve being reversible to allow for a fluid flow through said tubing in only a selected one of two opposing directions.

6. The method of lavaging defined in claim 2, wherein said container has a series of graduated markings on a surface thereof, indicative of a volume of a liquid within said container.

7. The method of lavaging defined in claim 2, wherein said container is comprised of a flexible plastic material.

8. The method of lavaging defined in claim 7, wherein said container includes an integrally formed handle at the upper end thereof.

9. The method of lavaging defined in claim 2, further comprising a handle attached to the upper end of said container.

10. The method of lavaging defined in claim 2, wherein each of said self-sealing ports includes a seal comprised of one of a plastic and rubber material, and wherein said breaching means comprises a hollow spike attached to the first end of said tubing, said spike being insertable through said seal to establish the fluid communication between the interior of said container and the interior of said tubing.

11. The method of lavaging defined in claim 2, wherein each of said self-sealing ports includes a valve, and wherein said breaching means comprises a device attached to the first end of said tubing, said device being insertable into said valve to open said valve and establish the fluid communication between the interior of said container and the interior of said tubing.

12. The method of lavaging defined in claim 2, wherein said container comprises two containers, said breaching device comprises two breaching means, and said tubing has essentially a Y-shape with first, second and third ends, with one of said breaching means being attached to the first end of said tubing for connection with the first self-sealing port of one of said containers, and the other one of said breaching means being attached to the third end of said tubing for connection with the second self-sealing port of the other one of said containers.

13. The method of lavaging defined in claim 2, wherein said container includes a resealable opening at the upper end thereof for filling said container with a liquid.

14. The method of lavaging defined in claim 13, wherein said resealable opening comprises a plurality of snap seals.

15. The method of lavaging defined in claim 13, wherein said resealable opening comprises a zipper-type seal.

* * * * *